United States Patent
Graser et al.

(10) Patent No.: US 11,249,078 B2
(45) Date of Patent: Feb. 15, 2022

(54) UNIVERSAL METHOD FOR DETECTING VARIOUS ANALYTES

(71) Applicant: IST Innuscreen GmbH, Berlin (DE)

(72) Inventors: Elmara Graser, Berlin (DE); Timo Hillebrand, Hoppegarten (DE)

(73) Assignee: IST Innuscreen GmbH, Berlin (DE)

( * ) Notice: Subject to any disclaimer, the term of this patent is extended or adjusted under 35 U.S.C. 154(b) by 277 days.

(21) Appl. No.: 14/903,228

(22) PCT Filed: Jul. 7, 2014

(86) PCT No.: PCT/EP2014/064444
§ 371 (c)(1),
(2) Date: Nov. 21, 2016

(87) PCT Pub. No.: WO2015/004057
PCT Pub. Date: Jan. 15, 2015

(65) Prior Publication Data
US 2017/0097341 A1     Apr. 6, 2017

(30) Foreign Application Priority Data
Jul. 6, 2013   (DE) ..................... 10 2013 213 279.4

(51) Int. Cl.
*G01N 33/543*    (2006.01)
*G01N 33/53*     (2006.01)
(Continued)

(52) U.S. Cl.
CPC ..... *G01N 33/54346* (2013.01); *C12Q 1/6823* (2013.01); *G01N 33/5308* (2013.01);
(Continued)

(58) Field of Classification Search
CPC ......... G01N 33/5308; G01N 33/54326; G01N 33/587; G01N 33/558; G01N 33/54313;
(Continued)

(56) References Cited

U.S. PATENT DOCUMENTS

2008/0085508 A1     4/2008   Wei et al.

FOREIGN PATENT DOCUMENTS

WO     WO 2007/133704 A2     11/2007

OTHER PUBLICATIONS

Zhang et al. Fluorescent bio-barcode DNA assay for the detection of *Salmonella enterica* serovar Enteritidis. Biosensors and Bioelectronics, 2009, vol. 24, pp. 1377-1381. (Year: 2009).*

(Continued)

*Primary Examiner* — Shafiqul Haq
(74) *Attorney, Agent, or Firm* — Grüneberg and Myers PLLC (57) ABSTRACT

The invention relates to a method for detecting various analytes, characterized by the following steps: a) providing separation particles containing, on their surface, firstly means of binding the analyte to be identified and secondly means of separating the analyte bound to the particles; b) providing identification particles firstly having, on their surface, means for binding the analyte to be identified and secondly containing on their surface or enclosed therein, means which are capable, after they have been detached or released from the particles, by virtue of their labeling, of generating a signal which serves for identification of the analyte; c) combining analyte, separation particles and identification particles; d) removing and washing the identification particles bound via the analyte by means of the separation particles; e) releasing the means which serve to identify the analyte, characterized in that the means which serve to identify the analyte are coupled reversibly to the identification particles and in that the identification molecules serve simultaneously for identification of the analyte and for detection.

16 Claims, 8 Drawing Sheets

Specification includes a Sequence Listing.

(51) Int. Cl.
*G01N 33/552* (2006.01)
*G01N 33/58* (2006.01)
*C12Q 1/6823* (2018.01)
*G01N 33/558* (2006.01)

(52) U.S. Cl.
CPC . *G01N 33/54313* (2013.01); *G01N 33/54326* (2013.01); *G01N 33/552* (2013.01); *G01N 33/558* (2013.01); *G01N 33/587* (2013.01)

(58) Field of Classification Search
CPC ........... G01N 33/54346; G01N 33/552; C12Q 1/6823; C12Q 2537/125; C12Q 2563/143; C12Q 2563/179; C12Q 2565/133

See application file for complete search history.

(56) References Cited

OTHER PUBLICATIONS

Thaxton et al. A bio-bar-code assay based upon dithiothreitol-induced oligonucleotide release. Anal. Chem. 2004, vol. 77, pp. 8174-8178 (Year: 2005).*
Goluch et al. A microfluidic detection system based upon a surface immobilized biobarcode assay. Biosens Bioelectron 2009, vol. 24, No. 8, pp. 2397-2403. (Year: 2009).*
International Search Report and Written Opinion dated Nov. 18, 2014 in PCT/EP2014/064444.
Byung-Keun Oh, et al., "A Fluorophore-Based Bio-Barcode Amplification Assay for Proteins", Small, vol. 2, No. 1, XP055149853, 2006, pp. 103-108.
Dietmar Knopp, et al., "Review: Bioanalytical applications of biomolecule-functionalized nanometer-sized doped silica particles", Analytica Chimica Acta, vol. 647, No. 1, XP055150144, 2009, pp. 14-30.

* cited by examiner

Step 1: Binding of the sample

Step 2: Magnetic separation

Step 3: Release of the double-labeled molecules, identification on a lateral flow strip.

Positive Probe - Positive sample

| Well | Fluor | Content | Sample | End RFU | Call |
|---|---|---|---|---|---|
| A01 | FAM | Unkn | 5x10^4 | 2304 | |
| A02 | FAM | Unkn | 5x10^5 | 2337 | |
| A03 | FAM | Unkn | 5x10^6 | 2302 | |
| A04 | FAM | Unkn | 5x10^7 | 2311 | |
| A05 | FAM | Unkn | 5x10^8 | 2369 | |
| A06 | FAM | Unkn | 5x10^9 | 3826 | |
| A07 | FAM | Unkn | 5x10^10 | 10028 | (+) Positive |
| A08 | FAM | Unkn | 5x10^11 | 64650 | (+) Positive |
| F12 | FAM | Neg Ctrl | | 2296 | |
| G12 | FAM | Neg Ctrl | | 2297 | |
| H12 | FAM | Neg Ctrl | | 2285 | |

Fig. 8A

1: biotin-FITC-labeling
2. biotin-DIG-labeling
3. both labeled molecules
4. negative control

Fig. 8B

Streptavidin    anti      anti      Biotin/
                FITC      DIG       BSA

UNIVERSAL METHOD FOR DETECTING VARIOUS ANALYTES

The present invention relates to a multiplexable method for amplification of a signal for detecting various analytes for medical, biological and biotechnological fields. The design of the method permits to carry out a detection of the analyte not only device-independent but also fully automatically.

STATE OF THE ART

Not only the molecular-biological diagnostics but also analysis and identification of nucleic acids, proteins, antibodies, immunogenic substances etc. have become a essential part of modern medical laboratory diagnostics, forensic diagnostics, veterinary medicinal laboratory diagnostics or food and environmental diagnostics.

Genetic diagnostics has been revolutionized with the invention of PCR technology (U.S. Pat. No. 4,683,202) which permits to multiply specifically any nucleic acid sequence. Another essential advantage was provided by the introduction of real-time PCR applications (U.S. Pat. No. 5,210,015, U.S. Pat. No. 5,716,784 and U.S. Pat. No. 5,487,972). Moreover, there are other enzymatic amplification processes, which are carried out at constant temperature, such as for example NASBA or Qβ replicase assays or other isothermal techniques (J. Compton Nature 350; 91-92; 1991, WO8706270, EP 1724362 A1 etc.) and which are used for the same objective. Further identification technologies are, among others, ELISAs for the identification of proteins or nucleic acids (R. Yalow et al. *J. Clin. Invest.* 39; 1157-75; 1960, Blotting Techniques for the Identification of Proteins and Nucleic Acids Southern (E. M. *J. Mol. Biol.* 98; 503-517; 1975, Alwine J C et al. *Proc. Natl. Acad. Sci. U.S.A* 74; 5350-5354; 1977, Renart, J. et al. *Proc. Natl. Acad. Sci. U.S.A.* 7; 3116-3120; 1979), Biochip Techniques for the Identification of Proteins and Nucleic Acids (e.g. WO 8808875), Lateral Flow Test Strips for the Identification of Proteins and Nucleic Acids (e.g. U.S. Pat. No. 4,956,302) or the identification by means of bio barcodes for Proteins and Nucleic Acids (US 20030054358 A1). Many of these identification methods require complex reagent mixtures including different enzymes for the amplification of signals for the identification of analytes (PCR, real time PCR, NASBA; ELISAs etc.). Moreover, a number of these techniques are suitable only for use for specific identification of nucleic acids, and cannot be used for the identification of proteins. Identification of proteins with respect to identification sensitivity is clearly more limited than the identification of nucleic acids by means of the techniques mentioned such as PCR or real time PCR.

Many of these methods are moreover coupled to expensive technical systems (PCR, real time PCR, bio barcodes) or require complex manipulation with the identification substances (ELISA, Blotting, Chip).

A universal possibility of identification for any analytes (proteins, nucleic acids etc.) exists with the bio barcode technology (Nature Protocols; Vol. 1, No. 1; 2006).

For the identification of nucleic acids said technology is based on a primary hybridization reaction of a target nucleic acid (fragmented DNA or RNA) to a capture oligonucleotide. Said capture oligonucleotide is covalently bound to a magnetic particle. After hybridization of the target nucleic acid with the capture oligonucleotide, magnet separation of the particles and washing steps occurs for removal of the unbound nucleic acids. In a second reaction step, the addition of gold particles occurs, which contain an oligonucleotide, which in turn can hybridize the target nucleic acid already bound to the capture nucleic acid of the magnetic particle. Moreover, the gold particles contain a so-called bio barcode DNA, and are therefore also called identification particles. After repeated separation of the complex magnetic particles—target nucleic acid—identification particles and further washing steps, the identification reaction occurs. For this purpose, the bio barcode DNA is released. This occurs, for example, in one embodiment, wherein the bio barcode DNA is bound to the gold particles via thiol groups, by the addition of DTT. The released bio barcode DNA in further steps is then hybridized to a solid phase, for example, a chip with a capture oligonucleotide partially complementary to the bio barcode DNA. Subsequently the addition of gold particles occurs which likewise carry an oligonucleotide partially complementary to the bio barcode DNA. This sandwich is then detected by the addition of silver ions by means of a scanner.

The identification of proteins occurs analogously wherein the magnetic particle is conjugated with a primary antibody which recognizes the protein to be identified. The identification particles (gold particles provided with hundreds of bio barcode DNAs) carry the secondary antibody. Again, a complex of magnetic particles with primary antibody—protein—gold particles with bio barcode DNA and secondary antibody is formed.

Magnetic separation and washing steps follow again. Detection occurs as in the case of identification of nucleic acids via release of the bio barcode DNA on an array.

Said technology is commercially available and associated with specific technical systems. (http://www.nanosphere.us/page/direct-detection-nucleic-acids).

Said tests are expensive and associated not only with the technical systems for final detection but also with the use of the chemicals (DTT) for detaching the barcode. Moreover the system requires a special identification technology in the form of hybridization of the released bio barcode DNA with a capture oligonucleotide as well as with gold particles and with subsequent silver enhancement which renders the process into a complex system with multiple steps.

A process developed further, which uses some principles of the bio barcode method, is based on the fact that the labeled barcode molecules exist already with a fluorescent labeling to be identified. Said identification molecules are specifically bound to gold particles via a thiol group. Detachment of the identification particles occurs again via the addition of DTT. Thus, said system is bound to gold particles. Other particle types are not possible. Moreover, identification of a fluorescent signal requires a very sensitive and expensive measurement technology, and therefore cannot be used for simple point of care applications (D. Zhang et al. Biosensors and Bioelectronics 24 (2009) 1377-1381).

In the published patent application US 2009/0005255 A1 a method is described which does not use gold particles but specific polymer particles. Said polymer particle assume the function of the gold particles as identification particles. Covalently bound DNA molecules exist on the polymer particles. The barcode molecules, which are used for the identification reaction, exist on the covalently bound DNA molecules (are hybridized to said molecules). Further nanoparticles are coupled to said barcode molecules. Said nanoparticles contain a magnetite core. The detection reaction occurs via a complicated measurement methodology for identification of a magnetic resonance. Thus, said process is likewise complex and associated with a complicated measurement technology and apparatus.

In another publication (US 2008/0268450 A1) a method is disclosed which is limited to an antibody-mediated identification. Instead of gold particles, silica particles are used which comprise amino-modified surfaces. The identification method (also a multiplex method) is based on sequence specific identification reactions of the barcodes, said method as well requiring several comprehensive and time-consuming work steps. The final identification occurs via a scanning electron microscope on a TLC chip. Thus, said method as well is complex and associated with an expensive device component.

US Patent Application US2006/0040286 A1 likewise describes a bio barcode method for identification of analytes. In this patent again gold particles are used. The barcodes must be detected via their specific sequence which renders the method complex and susceptible to faults. The final identification reaction occurs again on a chip surface via various steps, including silver deposition or fluorescence measurement. Hence, said method as well is mandatorily associated with an identification device, and moreover time-consuming and labor-intensive.

Objective of the Invention

The objective of the present invention is defined from the disadvantages mentioned of known identification systems. In particular, the method according to the invention shall be of easy implementation. Time expenditure shall be low. Moreover, the identification reaction shall also work without expensive technical systems and not require extremely complex measuring principles. Nevertheless, the method according to the invention shall comprise a multiplexing capability and sufficient sensitivity.

FIG. 7B shows a table of results corresponding to FIG. 7A.

FIG. 8A shows the results of the experiment of an example of multiplex detection of the identification particles.

FIG. 8B shows a schematic representation of a multiplex lateral flow strip.

Achievement of the Objective

The objective has been achieved in accordance with the features of the patent claims.

The method according to the invention permits a rapid signal generation without complicated equipment technology, a very high sensitivity, and is moreover equally suitable not only for the identification of nucleic acids but also for the identification of proteins or other immunogenic analytes. The detection can take place after a few steps on a simple test strip. Evaluation is done optically with the naked eye and does not require any complex, secondary identification reactions. Moreover, the method can be rendered fully automatically, multiplexable, and can be used as a closed, contamination-free system.

The method according to the invention for identification of an analyte likewise uses two specific particles—"separation particles" ("SP") as well as "identification particles" ("NP") wherein both particle types can comprise different shapes and sizes, preferably sizes between 1 nm and 10 μm. The identification particles need not be gold particles.

The separation particles are magnetic or paramagnetic particles (magnetic separation) or particles with a specific functionality permitting a separation process. The separation particles carry on their surface molecules or functional groups which can specifically interact with the analytes to be identified (capture molecules). Said particles may, if necessary, also be replaced by a solid phase which is coated with the same functional groups.

The identification particles can be comprised of different materials such as gold, latex, polymers or fullerenes etc. They do not possess any separation functionalities. Identification particles carry on their surface likewise molecules or functional groups (capture molecules) which can specifically interact with the analyte to be identified, with said molecules or functional groups recognizing a different and/or the same (in the case of several binding epitopes of the same type) target region (DNA sequence, epitope, protein sequence etc.) of the analyte to be identified. Moreover, the identification particles carry so-called identification molecules as this is also the case for the bio barcode DNA. The identification molecules can also be enclosed by the identification particles.

Said identification molecules serve to generate a detection signal in the detection process. In order that this is possible, the coupling of the identification molecules to the identification particle is such that it is a reversible coupling, i.e. the identification molecules can be separated again from the identification particle. This can be done chemically, physically or enzymatically or in a combination of said variants.

By the existing capture molecules on the separation particles and the identification particles, it is possible that both particles can highly specifically bind to an analyte. In order to avoid binding of several analytes to one and the same identification particle, it is appropriate to combine at first the separation particles to the analyte, and to add the identification particles only following the reaction. A simultaneous addition of the particles of both types to the analytes, however, is also possible.

The binding can be covalent, it may involve hydrogen bridges, it may involve antigen-antibody bindings etc.

By this interaction with the analyte, the connection between the separation particles and the identification particles with the analyte occurs, which permits a separation of the bound identification particles from the unbound identification particles. Thus, only, if the analyte exists in the particle mixture, the identification particles can be separated together with the separation particles. Otherwise, they remain in the solution.

Separation occurs in a manner dependent on the separation qualities of the separation particles and/or the separation surface (e.g. by magnetic separation of the magnetic particles).

As in the case of the bio barcode method, the detection reaction starts with release of the identification molecules from the identification particle. The inventive advantage of the method is disclosed as follows: contrary to the bio barcode technology, the identification molecules are preferably one or more DNA strands which are reversibly coupled to the DNA fragment covalently bound with particles (in the simplest case by hybridization). Contrary to all known methods, which are based on the principle of the bio barcode method, the identification molecules are characterized by an inventive differentness. Said DNA strands, which are responsible for the final identification reaction, are linked according to the invention with at least two labels each, of which at least one label is immunogenic, and, if necessary, one label permits a direct or indirect detection reaction. Due to the fact that the identification molecules are provided with two labels, it is possible to bind the identification molecules via a label to a solid phase, with the other label then being directly or indirectly used for detection. Thus, unlike the other bio barcode based methods mentioned, no further manipulation of the released identification molecules (e.g. hybridization etc.) is required which clearly simplifies the method.

Through the possibility of reversibly coupling several identification DNA strands to a DNA strand covalently bound to particles, sensitivity of the system can even be increased, since more labeled DNA is available for the identification reaction. The identification reaction based on detachment of the reversibly bound, labeled DNA strands is extremely simple and rapid and does not require any further equipment technology. It occurs, e.g., by the fact that a double-terminally (e.g. with FITC and biotin) labeled DNA is transferred to a test strip (lateral flow strip). Said test strip contains molecules complementary to the two labelings. The identification occurs by a test line on the strip subsequently becoming visible by use of known later flow techniques.

If a fluorescence measurement is desired, the DNA can be labeled with one or more fluorophores. But also chemical labeling groups resulting in a change of medium or enzymes can be used.

Figure 1:
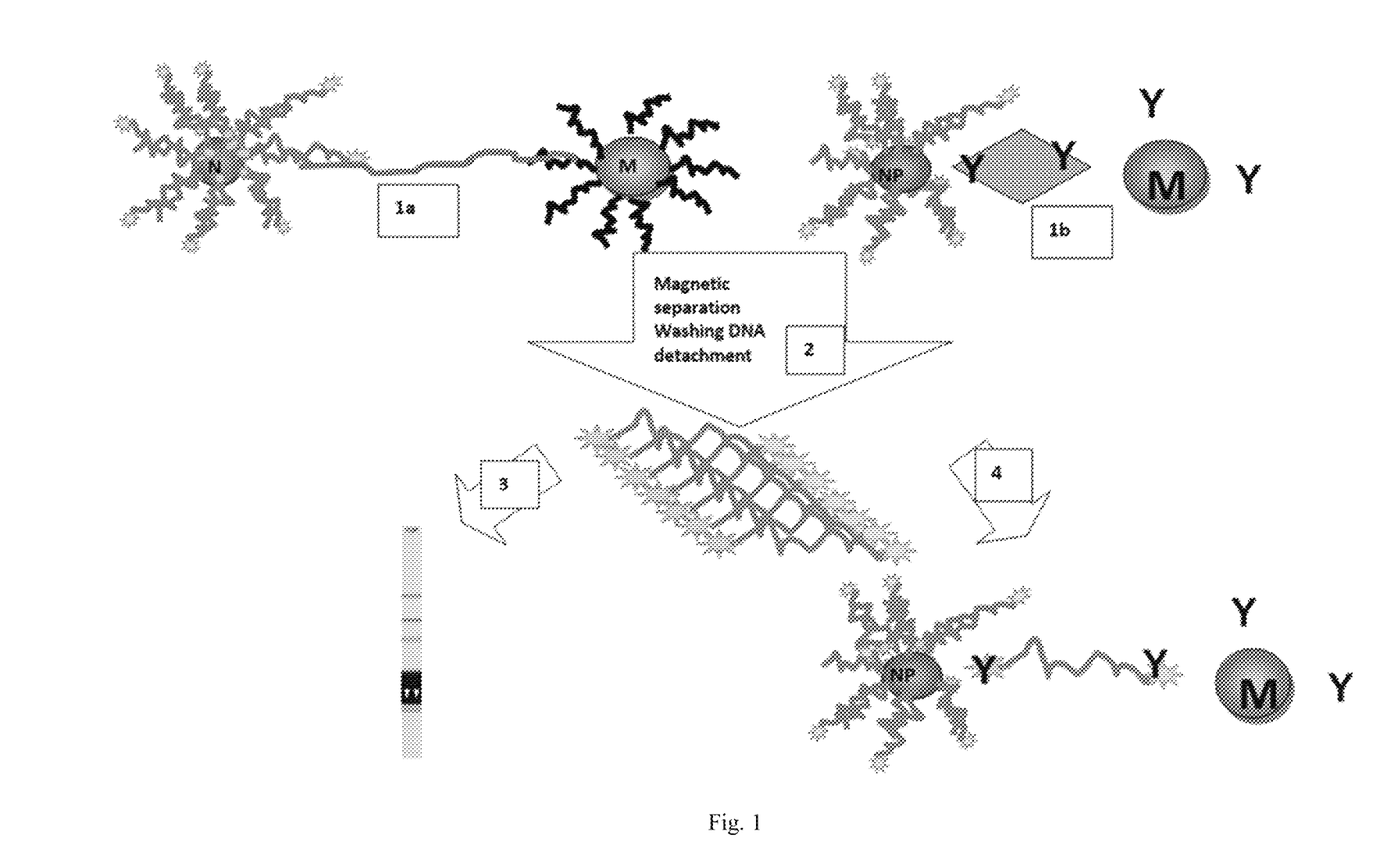
FIG. 1 shows a schematic representation of the method according to the invention.

After release of the identification molecules, identification of the previous reaction can occur within a few minutes. No complex processing and detection devices, as in the case of the bio barcode identification reaction, is required. The method according to the invention is schematically shown in FIG. 1.

As has already been described, in the bio barcode method the released bio barcode DNA in further steps is hybridized on a solid phase with a capture oligonucleotide partially complementary to the bio barcode DNA. Subsequently, addition of gold particles occurs, which likewise carry an oligonucleotide partially complementary to the bio barcode DNA. Said sandwich is then detected by addition of silver ions by means of a scanner. The alternative variants of the bio barcode technique mentioned in the publication likewise use very complicated measurement technologies and require expensive technical systems. No method can be read out on a classical lateral flow test strip.

As identification molecules not only DNAs can be used, but in principle any molecule that can be labeled can serve as an identification molecule. Preferably, two labelings exist on the identification molecule with one being immunogenic.

It is not only possible that the identification molecules exist on the surface of particles but the identification molecules can also (preferably) be enclosed by polymer particles, hence exist in a packaged state. Release then occurs by modification of the physical or chemical conditions (e.g. pH value, temperature).

The identification of the released identification molecules can—in the case of a DNA—also occur via an enzymatic amplification reaction, PCR, real time PCR or other isothermal techniques.

For increase of sensitivity, cascading of the reaction is possible.

According to the invention it is possible that siliceous particles are used on which the identification molecules are bound via spacers. It is also possible that magnetic particles are used as separation particles with magnetic core but siliceous shell.

Another advantage of the invention is to use particles which do not carry any specific interaction partner on the surface and bind analytes unspecifically. The binding can then occur either adsorptively or else via substances which can bind several substances.

Thus, it becomes obvious that the method according to the invention is clearly simpler in its implementation.

Nor will any device for identification be necessary. The test implementation thus also qualifies the method according to the invention in an ideal way as a potential point of care test system. The multiplexing capability exists due to different labeling of the reversibly associated molecules, as is shown later in an application example.

Another embodiment of the method according to the invention is based on the fact that the identification particles are polymer particles. Unlike the embodiment of the method according to the invention already described, the identification particles do not exist on the surface of the particles. On the surface are only those molecules or functional groups (capture molecules), which can specifically interact with the analyte to be identified, with said molecules or functional groups recognizing a different and/or the same (in the case of several binding epitopes of the same type) target region (DNA sequence, epitope, protein sequence etc.) of the analyte to be identified but not the identification molecules in the proper sense. The double-labeled identification molecules according to the invention (DNA strands) are reversibly enclosed in the polymer particle. This may be done by classical techniques of generation of polymer particles, as this is known for special packagings of pharmaceutical agents in polymer particles.

The identification reaction in the present embodiment is based on the fact that the identification molecules enclosed in the polymer particle are released again. This can be done by physical, enzymatic or chemical processes (e.g. modification of the pH value, temperature increases etc.). The identification molecules released are then used for the detection reaction in the manner already described (e.g. by means of a test strip). The embodiment that the identification molecules are enclosed in polymer particles and can be released also allows that the identification molecules can also be different. Apart from the double-labeled DNA strands, which are used for direct identification, also an unlabeled nucleic acid can be packaged. After the release reaction said nucleic acid can be used, for example, for classical duplication reactions (e.g. PCR or real time PCR), thereby permitting an extreme increase of sensitivity. Moreover, apart from the DNA also other molecules can be packaged, and used for detection after release (e.g. double-labeled oligomers which are no nucleic acid).

According to the invention the identification molecules released can both be directly identified and also serve as a target molecule for another signal amplification (cascading principle). In that case the identification molecules by means of their double labeling are bound to further separation and identification particles which comprise corresponding binding agents on their surface (e.g. anti-FITC antibodies and Streptavidin).

The method according to the invention discloses still further advantages compared with the bio barcode method and its known further developments (Goluch E D, Stoeva S I, Lee J S, Shaikh K A, Mirkin C A, Liu C. Biosens Bioelectron; 2009 Apr. 15; 24(8):2397-403).

In patent application no. US 20100081134A1 another bio barcode based method is described where as barcodes also the molecules hybridized to the covalently bound DNA fragments are used. But these are not linked with a label, hence are unlabeled. Said bio barcode DNAs are neither intended to bind to a nucleic acid target. Therefore, the following methodical disadvantages occur: the identification particles are likewise not labeled and can be identified only indirectly (chip-based or via a PCR), and the identification particles must be functionalized with two types of covalently bound DNAs—one for binding the target and the other for binding the barcode molecule (see FIGS. 13 A and B in US 20100081134A1).

Figure 2:
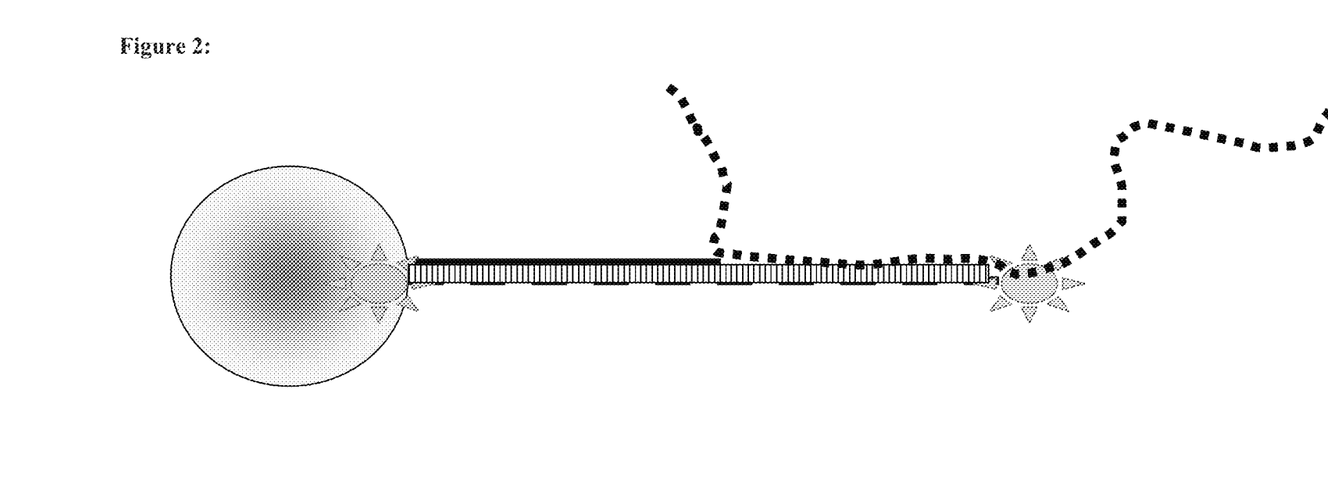
FIG. 2 shows a schematic representation of the binding of a nucleic acid analyte to the identification particles.
Figure 3:
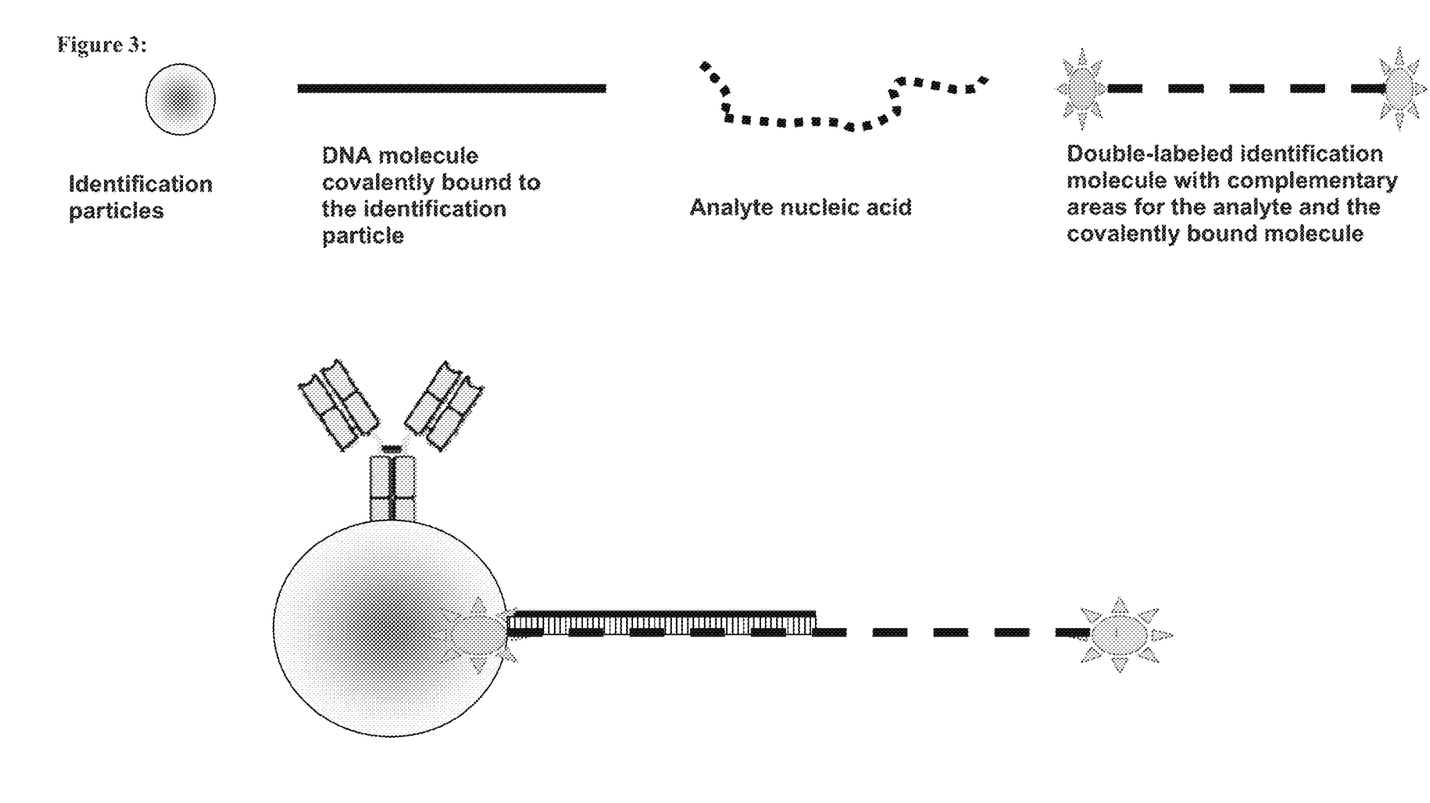
FIG. 3 shows a schematic representation of the functionalized identification particle.

But the method according to the invention, however, surprisingly permits also identification of nucleic acids (identification of a target DNA or target RNA). This happens by the fact that the identification molecules take the function of the capture molecules by partially hybridizing with the covalently bound DNA fragment as well as also partially bind complementarily to the target nucleic acid to be identified (FIG. 2) which is not possible with the bio barcode technology described.

The method according to the invention discloses still another important advantage which concerns the reproducible and controlled production of the particles used which contain the bio barcode DNAs. Barcode DNAs, which have not been washed out and hybridized during the production process, lead to false positive results in the identification reaction. Since these DNA molecules are not labeled, however, the particles after their coupling and the washing steps cannot be checked for purity. On the other hand, the method according to the invention permits an efficient control of the particles produced with respect to particle purity and particle functionality.

Another special embodiment of the method according to the invention permits a cascaded amplification of the detection sensitivity which is based on the fact that the identification molecules bound to the separated identification particles after their detachment or release according to the invention can act as target molecules in a second reaction cycle. For this purpose, the identification molecules released are combined with new identification particles and new separation particles, which in turn carry the capture molecules, which react with the identification molecules. The necessary conditions for binding the capture molecules of both particle types to the identification molecules are provided (temperature, pH-value etc.). By said binding an identification particle-identification molecule-separation particle-complex is created. The identification molecules bound to the separated, new identification particles are detached again, and can now be identified again or serve once again as analytes in the next identification cycle (cycle 3 and then cycle 4 etc.). Repetition of the cycles permits the cascade-like signal amplification whereby high sensitivity can be obtained.

The process of the detection method according to the invention, briefly summarized, is realized as follows (FIG. 1 Example—Procedure of the Method):

1. The analyte is combined with identification particles and separation particles. The necessary conditions for specific binding the capture molecules of both particle types to the analyte are provided (temperature, pH-value etc.). Through said binding an identification particles-analyte-separation particles-complex is created (process duration 10-20 minutes).

2. The complex described above is separated from the identification particle not bound to the analyte. Said separation is made possible by means of the binding capacity of the separation particles (for example, their magnetic capacities or specially attached separation molecules). The identification molecules bound to the separated identification particles are detached (or in the case of use of identification molecules packaged in polymer particles—release of the identification molecules). Process duration: 2-3 times washing (10 minutes), temperature-mediated detachment or release of packaged identification molecules (10 minutes).

3. The identification molecules obtained from the first cycle can be identified directly (detection time 10 minutes) or are combined with new identification particles and new separation particles. These carry per se the capture molecules which react with the identification molecules. The necessary conditions for binding the capture molecules of both particle types to the identification molecules are provided (temperature, pH-value etc.). Through said binding an identification particle-identification molecule-separation particle-complex is created.

4. The identification molecules bound to the separated new identification particles are detached. These serve as an analyte in the next identification cycle (cycle 3 and then cycle 4 etc.) and/or can be immediately detected, for example, without a device, with a lateral flow strip.

Repetition of the cycles permits the cascade-like signal amplification. The total work involved is 10-20 minutes or approximately 1 hour including incubation times.

Thus, the method according to the invention shows clear advantages compared with other bio barcode technology based methods. It is extremely simple and rapid in implementation. It does not require any equipment technology for detection measurement. It can be executed through several stages via cascading of the reaction process which results in an enormous increase of the detection sensitivity.

DEFINITIONS

Analyte and/or target: molecule to be identified, a group of molecules, a virus, a cell etc.

Capture molecules: molecules to be found on the identification molecules or their groups specifically binding (any type, hydrogen bridges, antigen-antibody, covalent etc.) to the analyte and/or the identification molecule.

Separation particles: magnetic or paramagnetic particles (magnetic separation) or particles with a special functionality permitting a separation process. The separation particles on their surface carry molecules or functional groups which can specifically interact with the analyte to be identified (capture molecules).

Particles: are particles of a size in the nm-μm range in any form, make-up and material (among others also fullerenes or polymers) which carry the capture molecules on their surface. Two types of particles are necessary:
1. Separation particles which are coated with capture molecules and, where applicable, separation molecules and in their structure offer a possibility of separating them from the reaction solution (for example, magnetically or by means of binding the separation molecules). In the method according to the invention said particles can also be replaced by a functionalized solid phase.
2. Identification particles which are coated with capture molecules and identification molecules or where the identification molecules are packaged and do not have an own ability for separation.
Separation molecules: the molecules which are, if applicable, on the surface of the separation particles, and which permit separation of said particles from the solution.
Identification molecules: are molecules, which at first are on the surface of the identification particles, but are then (physically or chemically) detached and on their part serve as signaling molecules for final identification. In another embodiment, the identification molecules are packaged into polymer particles and are released for the detection reaction. The identification molecules can be different substances, polymers, nucleic acid chains or individual molecules which are recognized not only by capture molecules but also by identification molecules of the final identification. Preferably, these are double-labeled DNA molecules of which at least one label is immunogenic and one label permits a direct or indirect detection reaction.
Final identification: can occur in different ways, for example, as a lateral flow identification, fluorescence detection, visual identification through a color change, enzymatic amplification techniques, electromagnetic measurement etc. The identification molecules and their labeling are built up according to the final identification.

The invention is presented below by means of the embodiments, with the embodiments not constituting a limitation of the method.

EMBODIMENTS

Example 1

Figure 4:
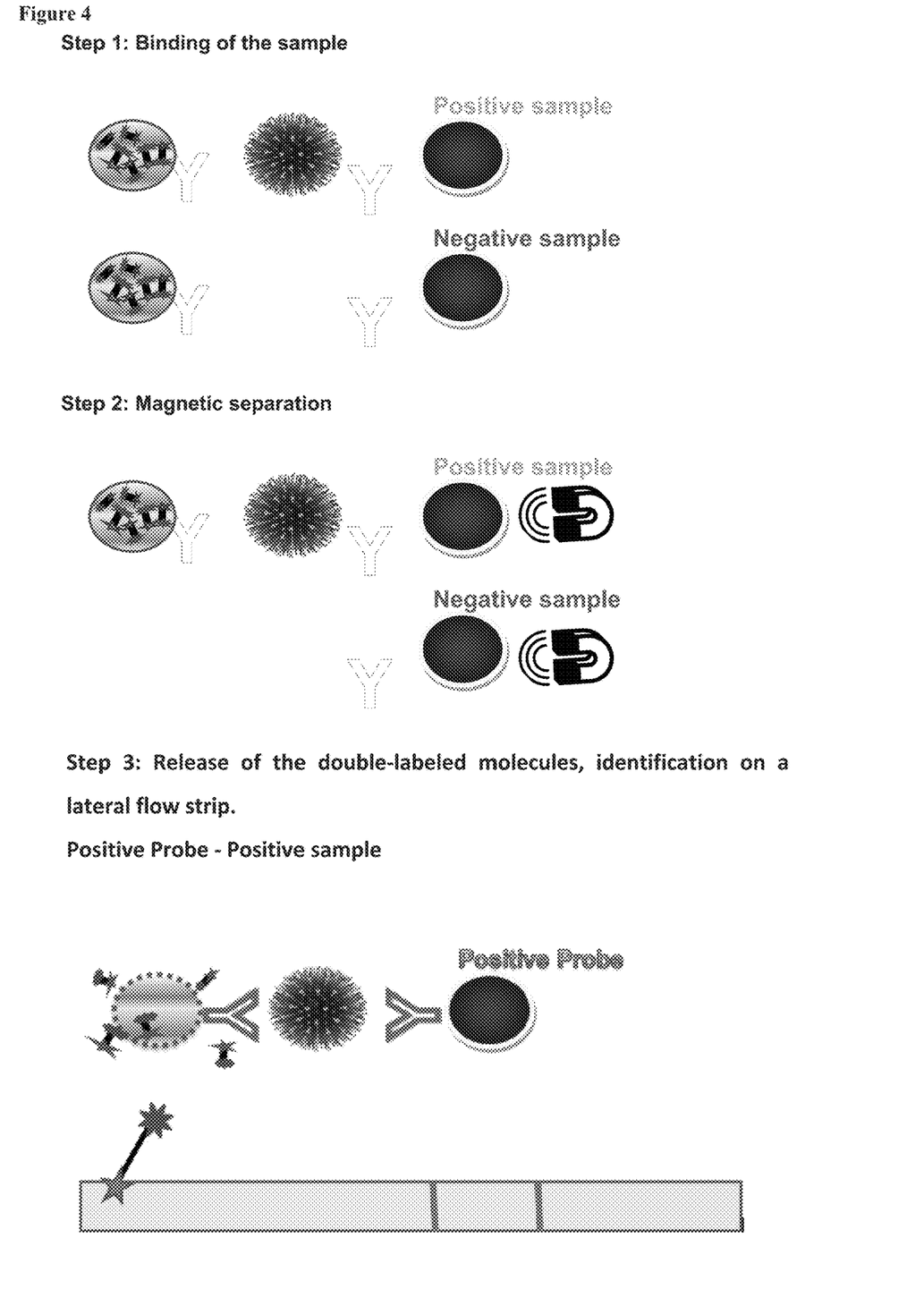
FIG. 4 shows a representation of the steps according to Example 2.
Figure 5A:
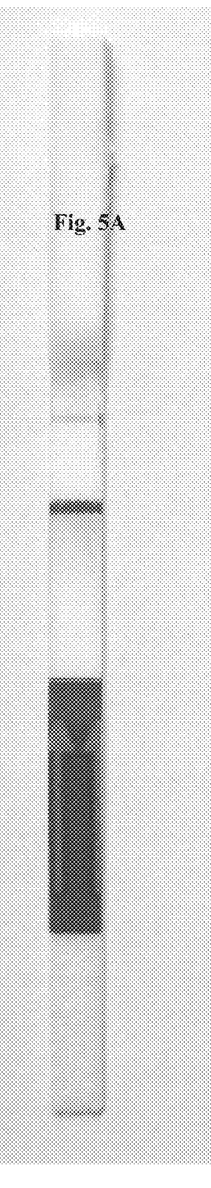
FIG. 5A shows a result of the lateral flow test in the process of production of the functionalized identification particles.
Figure 5B:
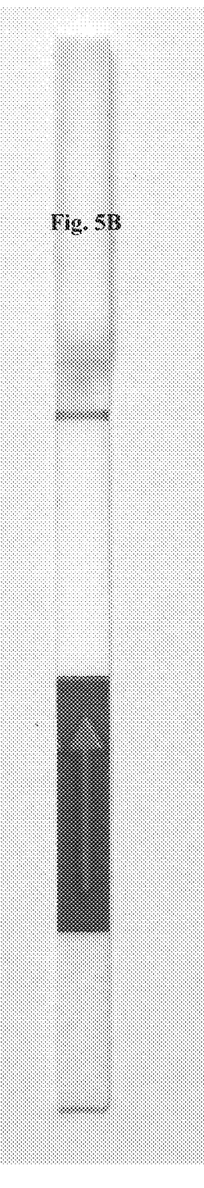
FIG. 5B shows a second result of the lateral flow test in the process of production of the functionalized identification particles.
Figure 5C:
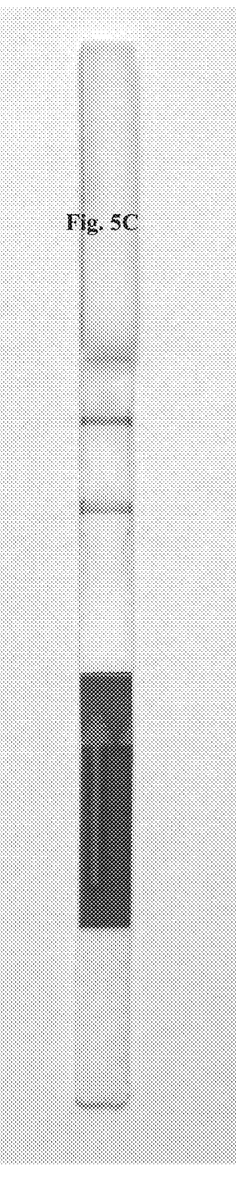
FIG. 5C shows a third result of the lateral flow test in the process of production of the functionalized identification particles.
Figure 6A:
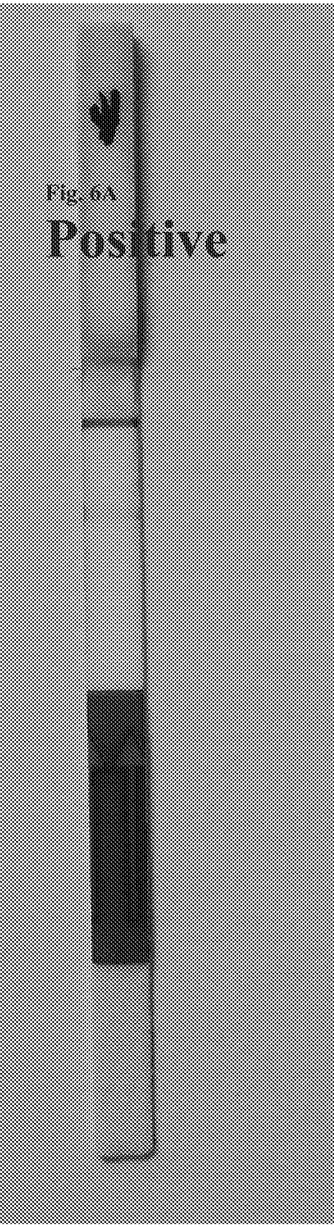
FIG. 6A shows the positive identification of a lower amount of yellow fever virus.
Figure 6B:
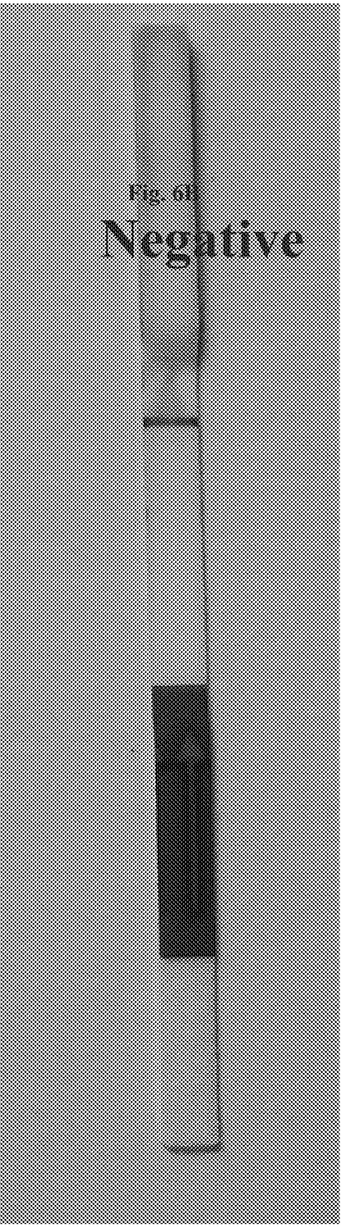
FIG. 6B shows the negative identification of a lower amount of yellow fever virus.
Figure 7A:
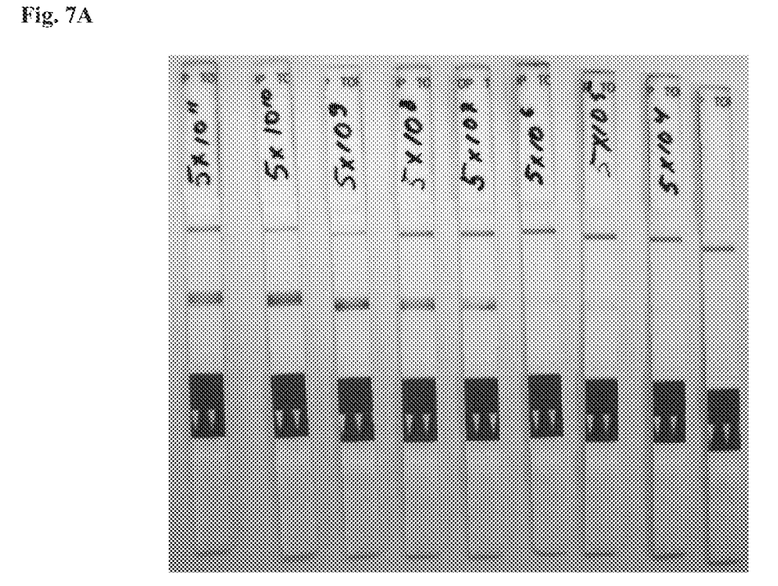
FIG. 7A shows a comparison of the detection sensitivity of a lateral flow strip with a fluorescent measurement.
Figure 7B:
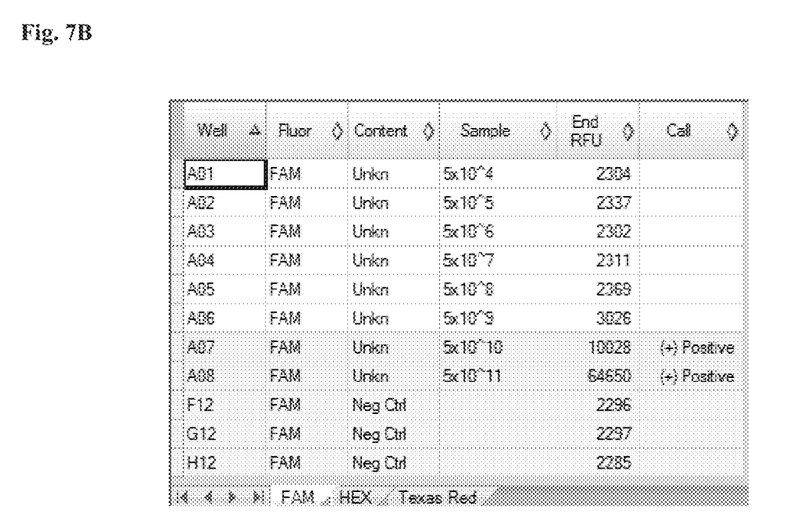
Figure 8A:
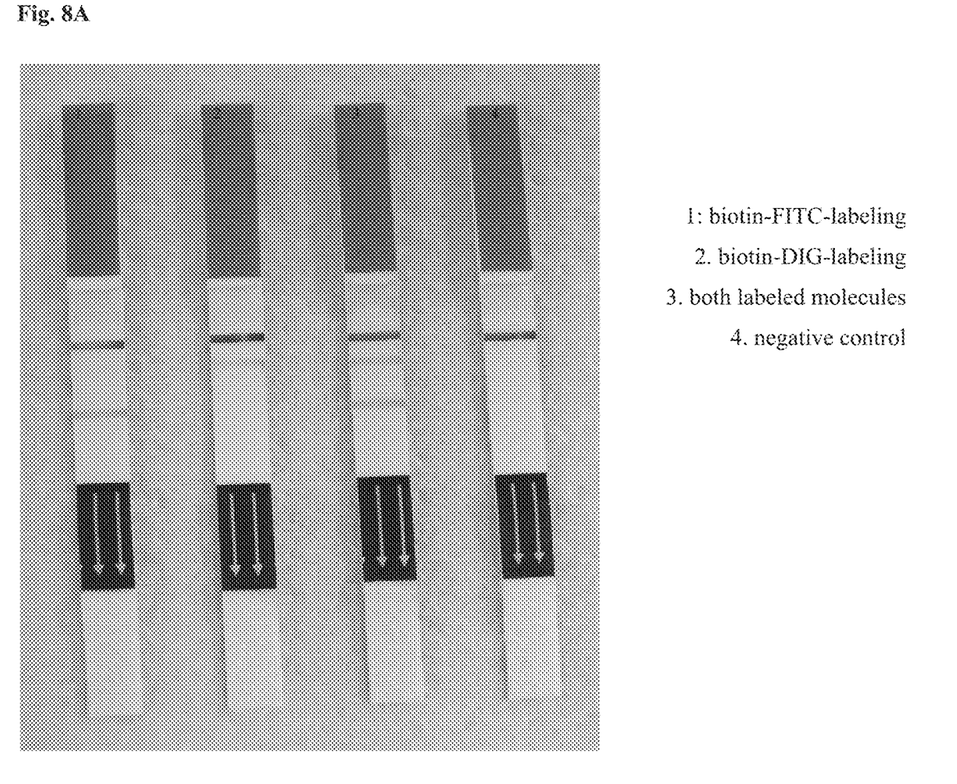
Figure 8B:
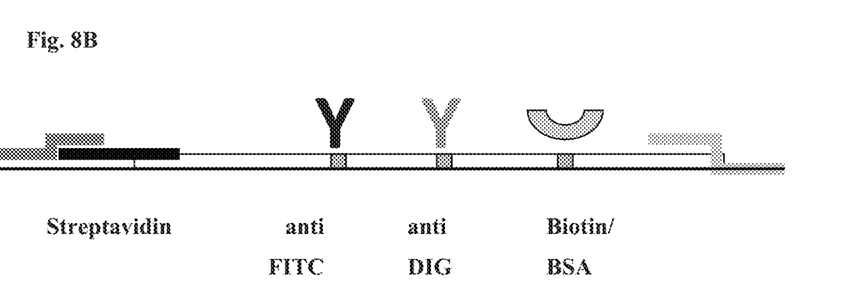

Production of the Identification Particles and Checking of their Purity and Functionality As identification particles, COOH functionalized polylactic acid particles with the size 500 nm have been used. A $NH_2$ coupled oligonucleotide ($NH_2$-GTG TTC GTG TCA TCT AGG AG) and an antibody against yellow fever virus are covalently bound to said particles. Binding occurred with a PolyLink-Protein Coupling Kit for COOH microparticles according to the instructions of the kit.

Subsequently the particles were washed and blocked with Tris-BSA.

As a next step, hybridization of the covalently bound oligonucleotide to the double-labeled identification molecule (FITC-TGC AGC AGG TGA TAA CCT TTG GCT CCT AGA TGA CAC GAA CAC-digoxigenin) followed. The bases shown in italics of the identification molecule are complementary to the covalently bound oligonucleotide. The identification particle functionalized with the antibodies and the oligonucleotides is schematically shown in FIG. 3.

The particles have been washed twice and subsequently chromatographically purified. Application of the particle supernatant onto a lateral flow strip with the binding domains for FITC and digoxigenin should supply information on the purity of the particles of the unbound, double-labeled identification oligonucleotide. On FIG. 4 (strip A) the strip is shown. The signal on the strip shows that the particles despite several washing and a chromatographic purification are not free of unbound identification molecules. The particles were continued to be washed with large volumes of Tris-BSA buffer until the supernatant showed no positive result on the lateral flow strip (FIG. 4; strip B).

Subsequently, it had to be shown that the identification particles despite several washings remain functional, hence that the double-labeled oligonucleotide is still hybridized to the oligonucleotide covalently bound to the particle. For this purpose, the purified identification particles were heated up to 70° C. in order to detach hybridization between the two oligonucleotides. The supernatant after heating was again applied onto a lateral flow strip. In that case, the lateral flow strip showed a positive result (FIG. 4; strip C) which proves that the identification particles on the one hand are clean and do not contain any more identification molecules (which leads to false positive results), on the other hand are functionally active for further identification.

The experiment demonstrated moreover the importance of the double-labeled identification molecules for process monitoring during production of the identification molecules.

Example 2

Vaccinia Virus Identification by Means of Functionalized Polymer Detection Particles with Enclosed Identification Molecules Nanocapsules, which do not present the double-labeled identification molecules on the surface but have these enclosed, serve as identification particles. Said polyester nanoparticles are produced by a direct miniemulsion by using the monomer 5,6-benzo-2-methylene-1,3-dioxepane (BMDO) and refunctionalized by carbodiimidazole couplings. Said production permits, apart from encapsulation of the DNA molecules, also an antibody binding on the surface of the nanoparticles. The identification particles differ from the other identification particles described only in that the identification molecules are now inside the particles and not on the surface. On the surface there is now only one antibody left. The identification particles and the separation particles are functionalized with anti-vaccinia virus antibodies. Identification of the vaccinia viruses occurs as described below. Detection particles and identification particles are introduced into the sample containing the vaccinia viruses:

Step 1: Formation of a complex from separation particles-virus-identification particles. A complex between the identification particles and separation particles and the vaccinia viruses is created. In the case of a target negative sample, no complex formation occurs and the identification particles as well as separation particles remain separated from each other.

Step 2: Magnetic separation. In the case of a positive sample, the complex formed (separation particles-virus-identification particles) is separated from the sample solution via magnetic separation, and subsequently washed twice in PBS, and briefly dried after a renewed separation.

Step 3: Release of the double-labeled molecules, identification on a lateral flow strip. A 15 minutes incubation at 85° C. generates a steam pressure within the identification particles which causes bursting of the particle walls and release of the double-labeled molecules. After the addition of water and a short vortex step, the particle supernatant is applied onto a lateral flow strip where the identification of the double-labeled molecules, and thus the identification of the existence of vaccinia viruses in the sample occurs.
The embodiment is schematically shown again in FIG. 4.

Example 3

Identification of a Small Amount of Yellow Fever Virus by Means of the Particles Produced According to the Invention As identification particles the particles produced in embodiment 1 have been used. As separation particles the COOH functionalized dextran-iron oxide-particles have been used. Said particles by means of the PolyLink-Protein Coupling Kit for COOH microparticles according the instructions of the kit were coupled with the same antibody as the identification particles. Yellow fever viruses from a viral culture were used as analytes. The concentration of the viruses was 1000 PFU/ml.

Reaction Batch:

| | Positive Sample | Negative Sample |
|---|---|---|
| Viral culture | 10 µl~100 PFU | — |
| 1xPBS | 100 µl | 200 µl |
| Identification particles | 5 µl | 5 µl |
| Separation particles | 5 µl | 5 µl |

Work Steps:

1. The reaction batch was incubated in 2 ml reaction vessels for 10 minutes at room temperature.
2. The reaction vessels were placed in a magnetic trap.
3. The sample supernatant was discarded.
4. The samples were washed twice in the magnetic trap.
5. After removal of the washing solution, 100 µl water were added to each sample.
6. The samples were removed from the magnetic trap and incubated for 10 minutes at 70° C.
7. The samples were placed again into a magnetic trap.
8. 5 µl of the supernatant were applied onto a lateral flow strip for detection of the released identification particles.

Total expenditure of time including incubation times 30 minutes max.

The results of the identification for a positive and a negative sample are shown in FIG. 5A-5C. As the result shows, direct identification of the yellow fever viruses could be carried out successfully with the process being characterized by its simplicity (no device is required) as well as by its high sensitivity and rapid performance.

Example 4

Comparison of the Identification Sensitivity of a Lateral Flow Test with a Fluorescence Measurement For the experiment, FAM-biotin labeled identification molecules were used where the FAM labeling can serve not only as an immunogen for an antibody binding a lateral flow strip but also as a fluorescent substance for a fluorescence measurement.

The identification molecules were measured in a dilution series (see table and FIGS. 7A and 7B). The fluorescence measurement occurred with a real time PCR device as an end-point measurement.

| Number of identification molecules | Lateral Flow Strip | End-point fluorescent measurement |
|---|---|---|
| $5 \times 10^{11}$ | positive | positive |
| $5 \times 10^{10}$ | positive | positive |
| $5 \times 10^{9}$ | positive | questionable |
| $5 \times 10^{8}$ | positive | negative |
| $5 \times 10^{7}$ | positive | negative |
| $5 \times 10^{6}$ | positive | negative |
| $5 \times 10^{5}$ | positive | negative |
| $5 \times 10^{4}$ | negative | negative |

The experiment showed that not only a detection without a device but also a detection of the identification particles based on the fluorescence measurement is possible. Moreover it could be demonstrated that the fluorescence measuring instruments common in laboratories have an approximately 10000-fold lower sensitivity than a lateral flow test without a device. Hence, the samples in other bio barcode based identification methods where fluorescence of the identification molecules is measured must operate with very expensive and sensitive technology in order to achieve the same sensitivity.

Example 5

An Example for a Lateral Flow Based Multiplex Detection of the Identification Particles In this experiment the identification particles were labeled with different labels. The results of the experiment and a schematic representation of a multiplex lateral flow strip are shown in FIGS. 8A and 8B.

Explanation on the Figures

FIG. 1 shows the principle of identification for nucleic acids and antigens:

1. Combining analyte, identification particles and separation particles.
2. Magnetic separation and washing of the unbound particles and molecules. Subsequent detachment of the identification particles.
3. Direct identification of the double-labeled identification particles on a lateral flow strip.
4. Cascade-like amplification reaction by a second identification cycle.

In FIG. 2 a schematic representation of the binding a nucleic acid analyte to the identification particles is shown. A schematic representation of the functionalized identification particle is shown in FIG. 3. The oligonucleotide complexes and antibodies shown are bound on the surface of the particle several times. FIG. 4 is a representation according to example 2.

Results of the lateral flow test in the process of production of the functionalized identification particles are shown in FIGS. 5A-5C. FIGS. 6A-6B shows the identification of a lower amount of yellow fever virus. The comparison of the detection sensitivity of a lateral flow strip (A) with a fluorescence measurement (B) is the subject matter of FIGS. 7A-7B. FIGS. 8A-8B shows the example of a multiplex detection of the identification particles.

The invention claimed is:

1. A method for detection of at least one analyte comprising:
 a) providing separation particles or a solid phase comprising on their surface i) a capture molecule for an analyte to be identified; and ii) means of separating the analyte bound to the particles;
 b) providing identification particles having on their surface a capture molecule for said analyte and at least one detachable identification molecule comprising a DNA molecule that is linked to at least two different labels capable of generating a signal which serves for identification of said analyte,
 c) combining said analyte, separation particles and identification particles,
 d) removing and washing said identification particles bound by said analyte which is bound to said separation particles; and
 e) releasing said at least one detachable identification molecule, wherein said at least two different labels are selected from the group consisting of a fluorophore, biotin, and digoxigenin, and
 wherein the capture molecule of the separation particle interacts with a different part of the analyte than the capture molecule of the identification particle.

2. The method according to claim 1, wherein said at least one identification molecule is labeled and serve as means for identification of the analyte, and wherein said at least one identification molecule is either reversibly coupled to nucleic acids, which in turn are bound irreversibly to a functionalized surface of the identification particles or are enclosed in the identification particles.

3. The method according to claim 1, wherein the identification particles comprise siliceous particles and are bound via spacers, or the separation particles comprise magnetic particles with a magnetic core but a siliceous shell.

4. The method according to claim 1, wherein the identification particles comprise a COOH functionalized surface to which $NH_2$ coupled nucleic acids are irreversibly bound.

5. The method according to claim 1, wherein said at least one identification molecule comprises at least one labeling permitting direct identification of nucleic acid molecules.

6. The method according to claim 1, wherein the fluorophore is selected from the group consisting of FITC and tamra.

7. The method according to claim 1, wherein the identification of the analyte occurs on a lateral flow strip or via a fluorescence measurement.

8. The method according to claim 1, wherein said at least one identification molecule carries one or more fluorophores for identification.

9. The method according to claim 1, wherein the analyte is at least one immunogen or nucleic acid.

10. The method according to claim 1, wherein the analyte is at least one nucleic acid and said at least one identification molecule simultaneously serves as a means for binding the nucleic acid analyte to be identified to the identification particles, and a separate means for binding the nucleic acid analyte to be identified to the identification particles is not present.

11. The method according to claim 1, wherein said at least one identification molecule serves as an analyte for signal amplification.

12. The method according to claim 1, wherein the separation particles are magnetic or comprise a functionality permitting a separation process.

13. The method according to claim 1, wherein the size of the particles ranges between 1 nm and 10 μm.

14. The method according to claim 1, wherein the identification particles comprise at least one of gold, latex, polymers or fullerenes.

15. The method according to claim 1, wherein the identification of the analyte occurs on a lateral flow strip.

16. The method according to claim 1, wherein the at least two different labels are selected from the group consisting of a fluorophore and digoxigenin.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: oligonucleotide detection molecule

<400> SEQUENCE: 1
gtgttcgtgt catctaggag         20

<210> SEQ ID NO 2
<211> LENGTH: 42
<212> TYPE: DNA
<213> ORGANISM: Artificial
<220> FEATURE:
<223> OTHER INFORMATION: oligotide detection molecule

<400> SEQUENCE: 2
tgcagcaggt gataaccttt ggctcctaga tgacacgaac ac         42